United States Patent [19]

Umezawa et al.

[11] Patent Number: 4,742,155

[45] Date of Patent: May 3, 1988

[54] PLIPASTATIN AND METHOD FOR PREPARATION THEREOF

[75] Inventors: Hamao Umezawa, Tokyo; Takaaki Aoyagi, Fujisawa; Tomio Takeuchi, Tokyo; Masa Hamada, Tokyo; Hiroshi Naganawa, Tokyo; Yasuhiko Muraoka, Tokyo; Takaaki Nishikiori, Tokyo, all of Japan

[73] Assignee: Zaidan Hojin Biseibutsu Kagaku Kenkyu Kai, Tokyo, Japan

[21] Appl. No.: 801,809

[22] Filed: Nov. 26, 1985

[30] Foreign Application Priority Data

Dec. 6, 1984 [JP] Japan .................. 59-256475

[51] Int. Cl.$^4$ .............................................. C07K 5/12
[52] U.S. Cl. .................................................. 530/317
[58] Field of Search ........................................ 530/317

[56] References Cited

PUBLICATIONS

Biological Abstrs., vol. 82 (1986) 95952; 95953; 95954.

Primary Examiner—Delbert R. Phillips
Attorney, Agent, or Firm—Banner, Birch, McKie & Beckett

[57] ABSTRACT

Plipastatin represented by the general formula

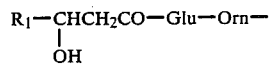

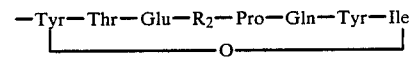

wherein $R_1$ is $-C_{13}H_{27}$ or $-C_{14}H_{29}$; and $R_2$ is Ala or Val, or salts thereof, which is prepared by culturing a Plipastatin-producing strain belonging to the genus Bacillus to produce and accumulate Plipastatin in a cultured broth and then isolating Plipastatin from the cultured broth. Plipastatin exhibits an enzyme inhibiting activity against phospholipase $A_2$, C and D and which will be useful as an immunosuppressive agent or as a type I anti-allergic agent.

7 Claims, 4 Drawing Sheets

PLIPASTATIN AND METHOD FOR PREPARATION THEREOF

BACKGROUND OF THE INVENTION

1. Field of the Invention

This invention relates to a new physiologically active substance, Plipastatin, which exhibits an enzyme inhibiting activity against phospholipase $A_2$, C and D and which will be useful as an immunosuppressive agent or as a type I anti-allergic agent.

2. Description of the Prior Art

Peptides having an acyl group are known and disclosed in, for example, Japanese Patent Unexamined-Publication (Kokai) No. 59-95252.

Adrenocortical steroids and cytotoxic immunosuppressors have been used as immunosuppressive agents. Also, anti-histaminics have been used as an anti-allergic agent.

All of the conventional immunosupressive agents have strong toxicity against hematopoietic organs in humans, so there has been a continuous need for the development of immunosuppressive agents having low toxicity. Since the human immune system is extremely complicated, immunosuppressive agents exhibiting new mechanisms of action are strongly desired. Also, the development of new drugs against type I allergic disorders is desired because there is no conventional drug that is capable of satisfactory inhibition of type I allergic reaction.

SUMMARY OF THE INVENTION

The present invention relates to a new physiologically active substance, Plipastatin, of the following general formula wherein $R_1$ is $-C_{13}H_{27}$ or $-C_{14}H_{29}$, $R_2$ is Ala or Val, and the abbreviations, Glu, Orn, Tyr, Thr, Pro, Gln, Ile, Ala and Val respectively mean glutamic acid, ornithine, tyrosine, threonine, proline, glutamine, isoleucine, alanine and valine. The present invention also relates to salts of Plipastatin and to a process for preparing Plipastatin and its salts. Plipastatin will be useful as an immunosuppressive agent or an anti-allergic agent which has low toxicity and exhibits a new mechanism of action.

BRIEF DESCRIPTION OF THE DRAWINGS

In the accompanied drawings.

DETAILED DESCRIPTION OF THE INVENTION

Figure 1:
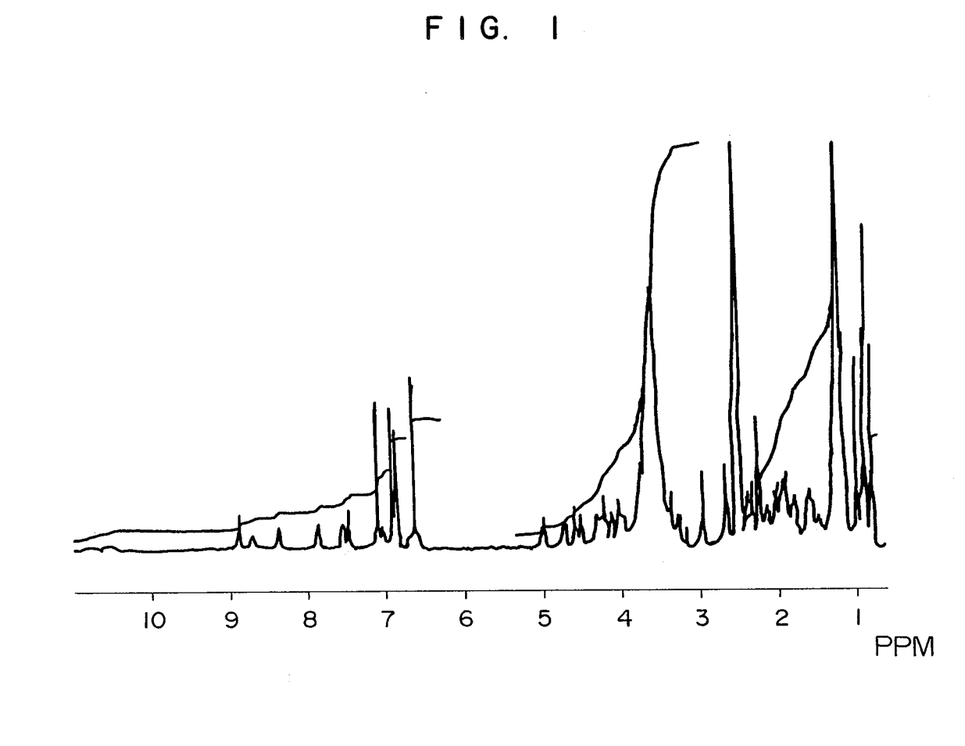
FIG. 1 is a NMR spectrum of Plipastatin $A_1$ of the present invention as measured in dimethyl sulfoxide-$d_6$ at 50° C.
Figure 2:
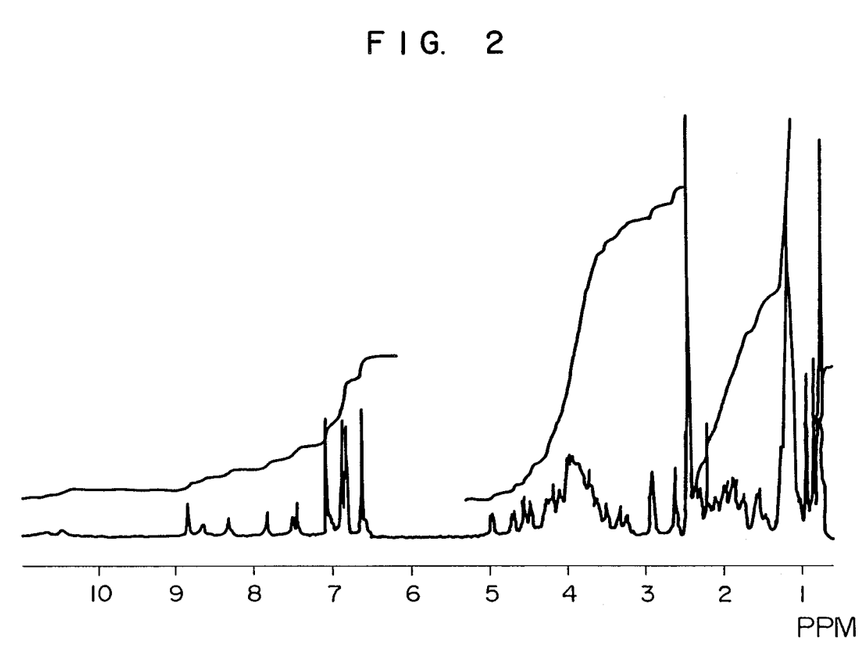
FIGS. 2, 3 and 4 are NMR spectrums of Plipastatin $A_2$, $B_1$ and respectively, as measured under the same conditions as in FIG. 1.
Figure 3:
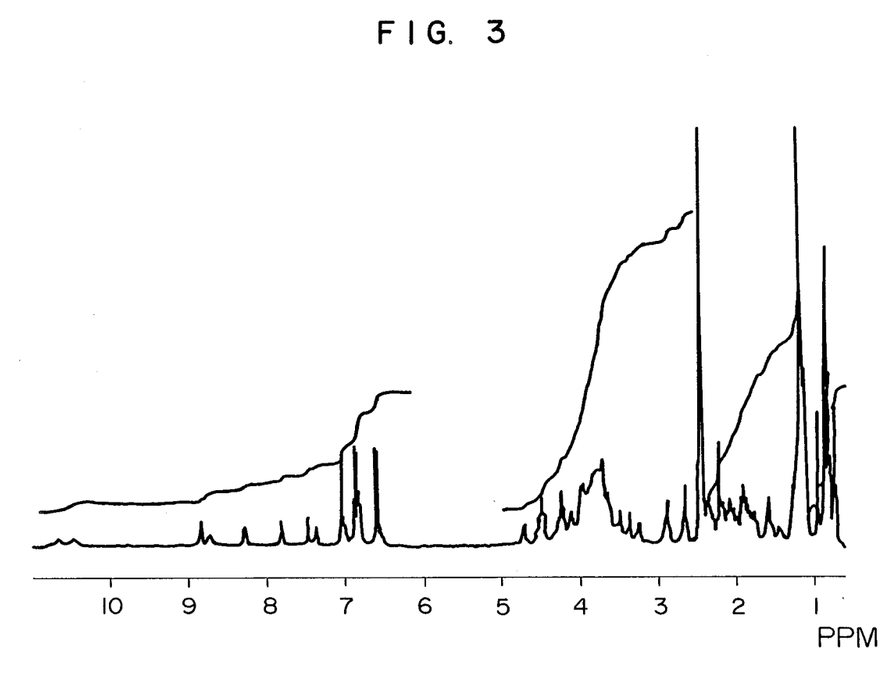
Figure 4:
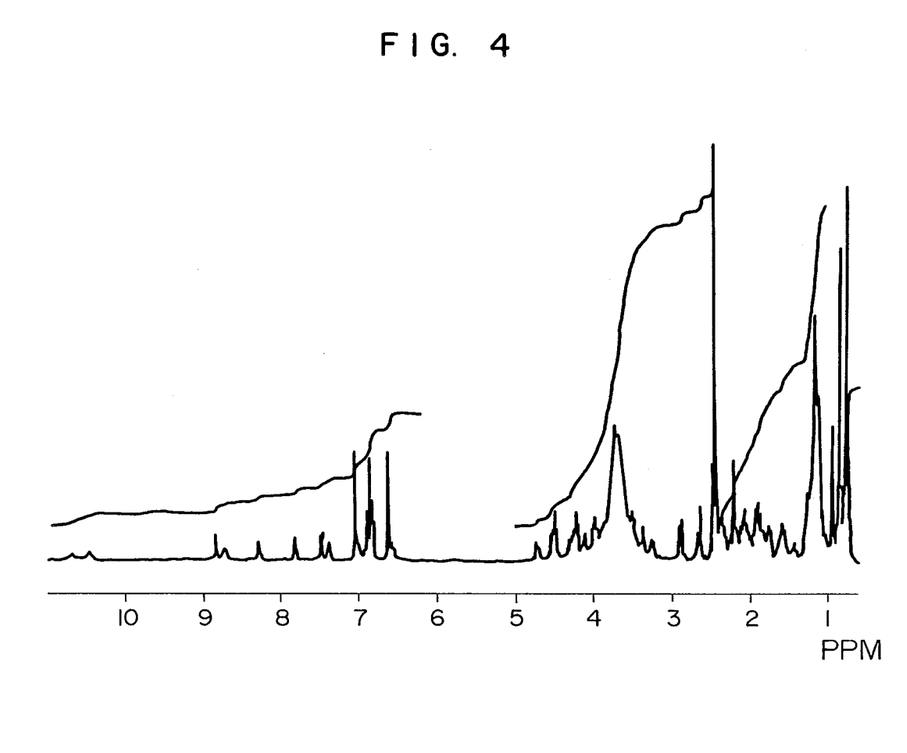

Plipastatin of the present invention includes the following four compounds. The compounds wherein $R_2$ in the formula I is Ala are hereunder referred to as Group A compounds and those wherein $R_2$ is Val, as Group B compounds:

The preparation of Plipastatin of the present invention is conducted by culturing a Plipastatin-producing strain belonging to the genus Bacillus to produce and accumulate Plipastatin in a cultured broth and then isolating Plipastatin from the cultured broth.

The term "Plipastatin-producing strain" used in this specification means those strains capable of producing at least one compound of the general formula I. Such strains include *Bacillus cereus* BMG302-fF67 isolated from a sample of the soil in the premises of the Institute of Microbial Chemistry, Shinagawa-ku, Tokyo. This strain was deposited with the Fermentation Research Institute, Agency of Industrial Science and Technology, Japan, on Sept. 12, 1984 and given the accession number FERM P-7843, then transferred on Nov. 8, 1985 to the deposit in said Institute under the Budapest Treaty on the International Recognition of the Deposit of Microorganisms for the Purpose of Patent Procedure, and given the accession number FERM BP-934.

The Mycological properties of the strain are described below.

Mycological properties of the strain BMG302-fF67

1. Cell morphology
   (i) Rod, having a size of approximately 1.0×2.6 microns.
   (ii) No specific polymorphism is observed.
   (iii) Motile, with peritrichous flagella.
   (iv) With ellipsoidal spores, which have a size of about 0.6×2.0 microns at the central position and are heat resistant. No swelling of the cell observed.
   (v) Positive in Gram's stain.

(vi) Non-acid fast.

2. Growth on various media (cultured at 30° C. except for the bouillon gelatin stab culture).

(i) Bouillon agar plate culture

Dull, opaque, substantially circular colonies having irregular, root-like periphery. Wrinkles appear on the surface of the colonies around the third day of the cultivation. No diffusible pigment.

(ii) Bouillon agar slant plate culture

The cell grows diffusively on the medium surface to form opaque, dull, pale yellowish brown colonies. Wrinkles appear around the third day of the cultivation to provide a dull surface. No diffusible pigment.

(iii) Bouillon liquid culture

The medium surface is covered with a pellicle on the first day of the cultivation and the cell starts to precipitate on the bottom of a test tube on the fifth day of the cultivation.

(iv) Bouillon gelatin stab culture

On the first day of the cultivation, a pellicle forms on the medium surface and a straitform gelatin liquefaction starts both at 20° C. and at 30° C. The liquefaction substantially completed on the seventh day of the cultivation.

(v) Litmus milk

Peptonization starts on BCP milk medium on the second day of the cultivation and completed on the seventh day. Alkaline reaction. No coagulation.

3. Physiological properties (The temperature of cultivation is 30° C. unless otherwise specified):

(i) Reduction of nitrate: positive (ii) Denitrification (by the method of Komagata et al): positive (iii) MR test: negative (iv) VP test: positive (v) Production of indole: negative (vi) Production of hydrogen sulfide: negative (vii) Hydrolysis of starch: positive (viii) Utilization of citric acid (on Koser's medium and Christensen's medium): positive (ix) Utilization of inorganic nitrogen sources (both potassium nitrate and ammonium sulfate): positive (x) Production of dye (King A and King B medium, Eiken): weak production of yellowish pigment (xi) Urease (urea medium, Eiken): negative (xii) Oxidase: negative (xiii) Catalase: positive (xiv) Growth range: growth between 10° and 37° C., no growth at 50° C., optimum growth between 27° and 37° C.; growth between pH 5.0 and pH 9.0, optimum growth between pH 6.0 and 8.0

(xv) Attitude toward oxygen: facultative anaerobic (xvi) O-F test (by the Hugh-Leifson's method): fermentation type (but no gas formation)

(xvii) Acid and gas formation from saccharides (on Hugh-Leifson's medium): negative for all saccharides

| Saccharides | BCP indicator | BTB indicator |
| --- | --- | --- |
| L-arabinose | − | − |
| D-xylose | − | − |
| D-glucose | − | + |
| D-mannose | − | − |
| D-fructose | − | + |
| D-galactose | − | − |
| Maltose | − | − |
| Sucrose | − | + |
| Lactose | − | − |
| Trehalose | − | − |
| D-sorbitol | − | − |
| D-mannitol | − | − |
| Inositol | − | − |
| Glycerol | − | − |
| Starch | − | − |

(xviii) Growth on the medium containing 7% NaCl: positive

To summarize the above properties, the strain BMG302-fF67 is a facultative anaerobic, gram-positive rod having spores, peritrichous flagella and motility. The spore is ellipsoidal and its position is central. It is heat-resistant. No swelling of the cell observed. Non-acid fast.

The strain produces opaque colonies with an irregular periphery on the agar medium; grows diffusively on the surface of the medium; liquefies gelatin; peptonizes milk; reduces nitrate; denitrification positive; MR test negative; VP test positive; does not produce indole or hydrogen sulfide; hydrolyzes starch; utilizes citric acid; urease reaction negative; oxidase reaction negative; catalase reaction negative; grows in the range of 10° to 37° C. (optimum range: 27° to 37° C.) at a pH between 5.0 and 9.0 (optimum pH range: 6.0 to 8.0); decomposes glucose fermentatively to form an acid; produces acids from D-glucose, D-fructose and sucrose, in such amounts that are positive to BTB indicator but negative to BCP indicator, but no gas evolves; no acid and gas formation from L-arabinose, D-xylose, D-mannose, D-galactose, maltose, lactose, trehalose, D-sorbitol, inositol, D-mannitol, glycerol and starch; and grows on the medium containing 7% NaCl.

According to "Bergey's Mannual of Determinative Bacteriology", 8th edition (R. E. Burhanan & N. E. Gibbons, The Williams Wilkins Company, Baltimore, 1974), these properties suggest that the strain BMG302-fF67 belongs to the genus Bacillus. The species, B. cereus, B. thurinqiensis, and B. coagulans that do not cause the swelling of cells at the spore formation, which are motile, produce asetoin from glucose and which do not produce any acid from L-arabinose, D-xylose, and D-mannitol, seem to be closely related to the strain BMG302-fF67. The strain BMG302-fF67 can be distinguished from B. thuringiensis because the latter is pathogenic to insects. (See Bergey's Manual, supra, p. 536.). The properties of the strain BMG302-fF67 are compared in the following table with those of B. cereus and B. coagulans. [See Bergey's Manual, supra, and "Igaku Saikin Dotei No Tebiki", 2nd edition, p. 197, Kindai Shuppan (This is a Japanese translation of Cowan & Steel "Cowan & Steel's Manual for the Identification of Medical Bacteria (2nd ed.)" by T. Sakasaki).]

| | Comparison of the properties of the strain BMG302-fF67 with those of closely related species | | |
|---|---|---|---|
| | | Species | |
| Properties | BMG302-fF67 | B. Cereus | B. coagulans |
| Form of spore | ellipsoidal | ellipsoidal or cylindrical | ellipsoidal or cylindrical |
| Swelling of cell at spore formation | − | − | + or − |
| Position of spore | center | center | center ~ end ~ near end |
| Acid formation   ⎫ from glucose | + | + | + |
| Gas formation    ⎭ | − | − | − |
| Asetoin formation | + | + | + or − |
| Cell size (microns) | 1.0 × 2.6 | 1.0~1.2 × 3~5 | 0.6~1 × 2.5~5 |
| Motility | + | d | + |
| Growth temperature | 10° C.~37° C. | 10–20° C.~35–45° C. | 12–25° C.~55–60° C. |
| Acid formation from L-arabinose, D-xylose and D-mannitol | − | − | d |
| Anaerobic growth | + | + | + |
| Reduction of nitrate | + | + | d |
| Gram-stain | + | + | + |
| Catalase | + | + | + |
| Hydrolysis of gelatin | + | + | − |
| Growth on the medium containing 7% NaCl | + | + | − |

(NOTE: + = positive in 90 to 100% of the samples)
(− = negative in 90 to 100% of the samples)
(d = positive in 11 to 89% of the samples)

As shown in the table, the strain BMG302-fF67 does not grow at 50° C. It is more similar to *B. cereus* than to *B. coagulans* in terms of the positive hydrolysis of gelatin and growth on the medium containing 7% NaCl. The strain is clearly distinguished from *B. coagulans* with respect to other properties as well. Thus, the strain BMG302-fF67 is identified as *Bacillus cereus* BMG302-fF67.

The method of the present invention is explained below in detail.

For producing Plipastatin by the method of the present invention, the strain described above is first cultured aerobically on a medium containing nutrients available for bacteria. Conventional nutrients utilized for the cultivation of bacteria can be used as nutrient sources. For example, polyalchol such as glycerin, carbohydrates such as saccharide, for example, glucose, lactose, sucrose, starch, maltose molasses, as well as fats may be used, singly or in combination, as carbon sources. Typical examples of inorganic and organic nitrogen sources which may be used include ammonium chloride, ammonium sulfate, urea, ammonium nitrate, sodium nitrate, peptone, meat extract, yeast extract, dry yeast, corn steep liquor, soybean meal, cotton seed oil cake, oatmeal, casamino acid, Bactosoytone, soluble vegetable proteins, and mixtures thereof. If necessary, inorganic salts such as sodium chloride, magnesium sulfate, copper sulfate, iron sulfate, zinc sulfate, manganese chloride, calcium carbonate and phosphates, as well as organic and inorganic substances capable of promoting the growth of the strain of the present invention and the formation of Plipastatin such as amino acids may be added.

The preferred method of cultivation is a liquid culture, particularly a submerged spinner culture.

The cultivation is desirably carried out at a temperature of 10° to 37° C., preferably 25° to 30° C. and at pH 5.0 to 9.0, preferably 6.0 to 8.0, more preferably an approximately neutral pH. The physiologically active substance Plipastatin is produced and accumulated in a cultured broth by conducting the cultivation, usually for one or two days, by the liquid culture method. The cultivation is stopped when the amount of Plipastatin produced in the cultured broth reaches a maximum. The cells are filtered off and then the product of interest is isolated from the resulting filtrate and purified.

The monitoring of the production of Plipastatin through the cultivation and purification steps is accomplished by measuring the antiphospholipase D activity in accordance with the following method.

The measurement of the antiphospholipase D activity is carried out by the method of Okuyama et al. described in A. Okuyama, T. Nishikiori, T. Aoyagi and H. Umezawa, Biochemistry international, 4, 417, 1982. Dipalmitoylphosphatidyl choline (DPC) (200 mM) and cholin-methyl-$^{14}$C-DPC ($4\times10^4$ dpm) are suspended ultrasonically in 390 μl of 50 mM tris-hydrochloric acid buffer (pH 5.7) containing 1 mM calcium chloride. To the resulting suspension is added 10 μl of a solution containing the sample to be tested. To the resulting mixture is added 100 μl of a solution of commercially available phospholipase D (derived from cabbage) and reacted at 37° C. for 20 minutes. The reaction is quenched by addition of 1.5 ml of a mixture of chloroform, methanol and conc. hydrochloric acid (2:1:0.02 v/v). To this mixture is then added 1 ml of 50% methanol containing 0.1% M potassium chloride and the mixture is stirred. Two layers are separated by centrifugation. The radioactivity (a) of choline liberated from the upper layer by the enzyme is measured. Also, the radioactivity (b) of the buffer free from the sample is measured as a blank test. The percentage inhibition of phospholipase activity is calculated according to the following formula: $[(b-a)/b]\times 100$.

IC$_{50}$ values correspond to the concentration of the samples giving a 50% inhibition.

The isolation and the purification of the product from the filtrate of the cultured broth may be performed by any conventional method used to isolate the metabolites of microorganisms from the filtrates of their cultured broth.

Plipastatin is soluble in water, methanol, ethanol, and n-propanol but insoluble or sparingly soluble in usual organic solvents such as acetone. Thus, Plipastatin may be purified by any method that is used for purifying water-soluble acidic substances. For example, adsorption onto and desorption from activated carbon powder or porous resins and column chromatography with silica gel, Silanised silica gel ® or Sephadex ® LH-20 may be used singly or in combination.

By way of example, the filtrate of the cultured broth of *Bacillus cereus* BMG302-fF67 is treated with Amberlite ® XAD-7 to adsorb the substance of interest. After washing with water, the resin is eluted with 80% methanol to obtain a crude brown powder containing the substance of interest. This contains the four compounds of Groups A and B of Plipastatin of the present invention.

The isolation of each compound is performed as follows:

A solution of the so-obtained crude powder in n-propanol is passed through a column of silica gel that has been equilibrated with n-propanol, followed by elution with an aqueous n-propanol solution with the stepwise increasing water content to separate Group A compounds ($A_1$ and $A_2$) from Group B compounds ($B_1$ and $B_2$) of Plipastatin to be defined hereafter. The so-obtained Plipastatin Group A may be chromatographed on Silanised silica gel ® preliminarily equilibrated with a mixture of an aqueous solution of 1% potassium acetate plus 3% acetic acid and methanol (4:6), followed by elution with the same solvent mixture to collect the fractions containing the product of interest. The fractions are then desalted with Sephadex ® LH-20, concentrated and freeze-dried. Thus obtained powder is then subjected to High Pressure Liquid Chromatography (HPLC) on a column preliminarily equilibrated with a mixture of one part of an aqueous solution of 2% potassium acetate plus 6% acetic acid and one part of acetonitrile. Each of the fractions containing the product of interest obtained by HPLC is treated with Sephadex ® LH-20 to remove potassium acetate contained therein, and then, the respective fraction are concentrated and freeze-dried to give a potassium salt of Plipastatin $A_1$ or $A_2$ as a white powder.

Also, Plipastatin Group B (including $B_1$ and $B_2$) obtained by said column chromatography on silica gel is chromatographed on Silanised silica gel ® preliminarily equilibrated with 40% methanol solution, followed by elution with the same methanol solution to collect the fractions containing the product of interest, which are then desalted with Sephadex ® LH-20, concentrated and freeze-dried. The resulting powder is subjected to the same HPLC as used in the separation of Group A compounds, thereby separating Plipastatin $B_1$ from $B_2$. The fractions containing Plipastatin $B_1$ or $B_2$ are treated with Sephadex ® LH-20, concentrated and freeze-dried to give a potassium salt of Plipastatin $B_1$ or $B_2$ as a white powder.

The respective compound of the present invention so obtained was saponified with an alkali and subjected to mass-spectrometry. The fragments of molecular ions appearing on the spectrum show that each of the compounds has the following amino acid sequence from N-end: Glu, Orn, Tyr, Thr, Glu, Ala, (or Val), Pro, Gln, Tyr and Ila. Also, the existence of a lactone ring appearing on the IR spectrum shows that Tyr connected with Orn is bonded to C-end amino acid, Ile, and this is supported by enzymolysis and NMR spectrum. On the basis of these data, the present inventors identified the structures of the compounds of the present invention as above.

The physicochemical properties of the compounds of the present invention are summarized in Table 1 below. (All measurements were carried out using potassium salts of the compounds unless otherwise specified.)

TABLE 1

| | Physicochemical properties of Plipastatin | | | |
|---|---|---|---|---|
| | $A_1$ | $A_2$ | $B_1$ | $B_2$ |
| Melting point (°C.) | 193–195° C. | 188–190° C. | 186–187° C. | 184–186° C. |
| Molecular weight of free type (potassium salt) | 1462 (1578.00) | 1476 (1592.03) | 1490 (1529.87) | 1504 (1543.90) |
| Elemental Analysis (%) | C 54.44, H 7.46 N 9.78, K 6.86 | C 54.67, H 7.86 N 10.84, K 6.64 | C 58.07, H 7.54 N 11.07, K 3.24 | C 58.50, H 7.84 N 10.63, K 3.13 |
| Molecular formula (potassium salt) | $C_{72}H_{110}N_{12}O_{20}$ ($C_{72}H_{107}N_{12}O_{20} \cdot K_3$) | $C_{73}H_{112}N_{12}O_{20}$ ($C_{73}H_{109}N_{12}O_{20} \cdot K_3$) | $C_{74}H_{114}N_{12}O_{20}$ ($C_{74}H_{113}N_{12}O_{20} \cdot K_1$) | $C_{75}H_{116}N_{12}O_{20}$ ($C_{76}H_{115}N_{12}O_{20} \cdot K_1$) |
| $UV^{MeOH}_{\lambda max}$ ($\epsilon$) | 276 (1923) | 276 (1781) | 276 (1707) | 276 (1820) |
| IR (KBr $cm^{-}$) | 3350, 3050, 2970, 2935, 2860, 1760, 1660, 1550, 1520, 1455, 1405, 1355, 1310, 1250, 1205, 1175, 1140, 1100, 1025, 835 | 3350, 3050, 2970, 2935, 2860, 1760, 1660, 1550, 1520, 1455, 1405, 1355, 1310, 1250, 1205, 1175, 1140, 1100, 1025, 835 | 3350, 3050, 2970, 2935, 2860, 1760, 1660, 1550, 1520, 1450, 1400, 1355, 1305, 1260, 1245, 1205, 1175, 1140, 1100, 1025, 805 | 3350, 3050, 2970, 2935, 2860, 1760, 1660, 1550, 1520, 1450, 1400, 1355, 1305, 1260, 1245, 1205, 1175, 1140, 1100, 1025, 805 |
| Solubility | Soluble in water, methanol, ethanol, and dimethyl sulfoxide. Insoluble in organic solvents such as acetone, ethyl acetate, chloroform and benzene. | | | |
| Color reaction | Positive with ninhydrin, Rydon Smith, sulfuric acid and iodine. | | | |
| $R_f$ values a of TLC* b | 0.24 0.21 | 0.24 0.21 | 0.33 0.32 | 0.33 0.32 |
| Amino acid analysis of acid hydrolyzate (molar | Thr (1), Glu (3), Pro (1), Ala (1), Ile (1), Tyr (2), Orn (1), Ammonia (1) | Thr (1), Glu (3), Pro (1), Ala (1), Ile (1), Tyr (2), Orn (1), Ammonia (1) | Thr (1), Glu (3), Pro (1), Val (1), Ile (1), Tyr (2), Orn (1), Ammonia (1) | Thr (1), Glu (3), Pro (1), Val (1), Ile (1), Tyr (2), Orn (1), Ammonia (1) |

TABLE 1-continued

| | Physicochemical properties of Plipastatin | | | |
|---|---|---|---|---|
| | $A_1$ | $A_2$ | $B_1$ | $B_2$ |
| ratio)** | | | | |

Table 1. NOTE:
*Using silica gel thin layer (Kieselgel 60F 0.25 mm., Merck); developing solvents:
(a) n-butanol/acetic acid/water (4:1:1, v/v)
(b) 80% n-propanol
**Acid hydrolysis: 6 N HCl, 105° C., 18 hours in a sealed tube.

Acute toxicity

The compounds of the present invention have relatively low toxicity. For example, the acute toxicity test in mice showed that $LD_{50}$ value of Plipastatin $B_1$ was in the range of 250 to 500 mg/Kg (i.p.).

This supports that Plipastatin of the present invention can suppress an immuno response even if it is used alone. Thus, the compounds of the present invention will be useful as immunosuppressive drugs.

The compounds of the present invention are used as immunosuppressive drugs commonly in the form of alkaline metal salts or other non-toxic salts. The compounds of the present invention may be formulated and administered by conventional methods. They can be formulated into, for example, injections, powders, granules, tablets and suppositories. The route of administration of the compounds include, for example, parenteral, oral, and rectal.

In the formulation procedures, any pharmaceuturically acceptable carriers and other additives which do not affect the compounds of the present invention may be used. The amount of the active ingredient present in the formulation depends on the form of formulations, but generally ranges from 0.01% (w/w, hereunder the same) to 100%, preferably, 0.1 to 70%.

In the formulation procedures, any formulating aids which do not affect the compounds of the present invention, that is, carriers and other additives such as stabilizer, preservatives and analgesic agents may be used as required. The method of formulating injections is specifically described below.

The compounds of the present invention and mannitol are dissolved into distilled water and the resulting solution is filled into vials or ampules for injections or freeze-dried as such. Just prior to use, the freeze-dried powder can be reconstituted with physiological saline or distilled water to form injections.

The dose of the compounds of the present invention depends on such factors as the severity of the disease, but generally it is in the range of 0.01 to 2000 mg, preferably 0.1 to 1000 mg per day in an adult.

Typical examples of formulations are described below.

Injections

Thirty parts by weight of a potassium salt of Plipastatin $B_1$ is dissolved in 970 parts by weight of purified water and the resulting solution is sterilized by filtration through a milipore filter of GS-type. A 2-ml portion of the filtrate is charged into a 10 ml vial and freeze-dried to obtain a freeze-dried powder for injections.

Granules

Fifty parts by weight of a potassium salt of Plipastatin $A_1$, 600 parts of lactose, 330 parts of crystalline cellulose and 20 parts of hydroxypropyl cellulose are well mixed and the resulting mixture is compressed by using a Roller compactor ®, ground and sieved to collect granules having a particle size between 16 and 60 mesh.

Activity

The physiological activities of the new physiologically active substance, Plipastatin, of the present invention are explained below.

(1) Inhibition of phospholipase

The measurement of the inhibition of phospholipase was accomplished by the method of Okuyama et al. set forth above. The results are summarized in Table 2 below.

TABLE 2

| | Inhibition of phospholipase | | | |
|---|---|---|---|---|
| | Degree of inhibition, $IC_{50}$ (µg/ml) Plipastatin | | | |
| Phospholipase | $A_1$ | $A_2$ | $B_1$ | $B_2$ |
| $A_2$ | 4.3 | 3.4 | 5.2 | 3.5 |
| C | 1.9 | 4.0 | 3.6 | 4.5 |
| D | 2.1 | 3.8 | 2.8 | 3.3 |

(2) Immunosuppressive activity

As a result of studying the pharmacological effects of Plipastatin of the present invention, it was found that this substance has suppressive effects on cell-mediated immunity.

The suppressive effects on the cell-mediated immunity of both Plipastatin $A_1$ and Plipastatin $B_1$ of the present invention are illustrated by the following experiments.

Experiment 1

This experiment illustrates the effects on the cell-mediated immunity in normal mice.

The activities of Plipastatin $A_1$ and $B_1$ on cell-mediated immunity were studied in terms of delayed-type hypersensitivity (DTH) caused by inoculating mice with antigenic sheep red blood cells (SRBC) in one footpad (Reference: J. Exp. Med., 139, 1529-1539, 1974).

$CDF_1$ mice (female, 8 week of age) were inoculated intravenously with a suspension of $5 \times 10^5$ SRBC in physiological saline. At the same time, a single dose of an aqueous solution of 5 mg/Kg or 0.5 mg/Kg of Plipastatin $A_1$ or $B_1$ was administered intraperitoneally to the mice. Four days after the injection, the mice were subjected to the secondary challenge by subcutaneous injection of the other footpad with a suspension of $10^8$ SRBC in physiological saline. Twenty-four hours later, the degree of footpad swelling (increasing in the thickness of the footpad) was measured with a caliper. The cell-mediated immunity suppressive effects of the test compounds were determined by comparing the degree of footpad swelling in the treated animals with the degree of footpad swelling (100%) in untreated, control animals that were subcutaneously injected in their footpads with an aqueous solution of SRBC in physiological saline in stead of the test compounds. The results are summarized in the following table.

TABLE 3

| Plipastatin | Dose (mg/Kg) | Thickness of footpad × $10^{-2}$ mm | Percentage with respect to the control (%) |
|---|---|---|---|
| $A_1$ | 5 | 48 ± 16 | 49 |
|  | 0.5 | 63 ± 25 | 64 |
| $B_1$ | 5 | 57 ± 31 | 58 |
|  | 0.5 | 97 ± 44 | 99 |
| Control | — | 98 ± 43 | 100 |

Experiment 2

This experiment illustrates the suppressive effects of Plipastatin on the reaction of lymphocyte blastogenesis.

The reaction of lymphocyte blastogenesis was evaluated in terms of the incorporation of [$^3$H]-thymidine in the DNA synthesis by both T-cells and B-cells stimulated with concanavalin A (hereunder referred to as Con A) and lipopolysaccharide of E. coli 055:B$_5$. (Reference "Meneki Jikken Sosaho", or "Immunological Experiments Manual", pp. 2267–2276, The Japanese Society for Immunology).

In the reaction of T-lymphocyte blastogenesis, the T-cells were obtained by passing spleen cells of BALB/c mice (19 weeks old) through a nylon column to remove adsorptive cells and by then cultivating the resulting spleen cells in a plastic Petri dish for one hour to eliminate the remaining adsorptive cells. The cultivation of the T-cells was conducted in wells of a Falcon microtest plate using RPMI 1640 medium containing 20% fetal bovine serum, 25 ml of Hepes, 100 μg/ml of streptomycin and 100 U/ml of penicillin G. The T-lymphocytes (1×10$^5$), 5 μg/ml of Con A and PLIPASTATIN A$_1$ or B$_1$ were added in that order to the wells and said medium was then added to the wells to make a total of 0.2 ml. The resulting mixture was incubated for 72 hours. The mixture was pulse-labeled with [$^3$H]-thymidine at 8 hours before terminating the cultivation. The reaction of B-lymphocyte blastogenesis was performed following the same conditions as set forth above except that the spleen cells were substituted for the T-cells and that 100 μg/ml of LPS was used in place of the Con A.

Plipastatin A$_1$ at a concentration of 100 μg/ml suppressed the uptake of [$^3$H]-thymidine into the Con A-stimulated T-lymphocytes and the LPS-stimulated B-lymphocytes by 52% and 15%, respectively. Also, Plipastatin B$_1$ blocked the Con A-stimulated reaction of T-lymphocyte blastogenesis and the LPS-stimulated reaction of B-lymphocyte blastogenesis by 54% and 20%, respectively.

These data show that Plipastatin is a substance capable of suppressing the cell-mediated immunity in normal animals.

(3) Inhibition of PCA reactions

The study on the pharmacological effects of Plipastatin showed that it has suppressive effects on PCA (Passive Cutaneous Anaphylaxis) reactions.

The following experiments will demonstrate the suppressive effects of Plipastatin A$_1$ of the present invention on PCA reactions.

Experiment 1

This experiment shows the suppressive effects of Plipastatin A$_1$ on PCA reactions. The experiment described below was accomplished in accordance with conventional methods. (Reference: J. Immunology, 106, 1002–1011, 1971). Rats were sensitized with egg albumin antigen to obtain an anti-serum. The rats of the S-D strain (male, 8 wk of age) were passively sensitized by intradermal injection of 50 μl of the thus obtained anti-egg albumin serum on their backs. Forty-eight hours later, each rat was challenged by the intravenous injection of physiological saline containing egg albumin (2.5 mg) plus Evans blue (2.5 mg). Sixty minutes after the injection, any development of blue dye patch due to the extravasation of Evans blue at the sensitized site was checked. Five minutes before the challenge, the test compound (150 μl) was intradermally injected at the sensitized site. DSCG (disodium cromoglycate) was used as a control. The test results are summarized in Table 4 below.

TABLE 4

| Agents | Conc. (μM) | Development of blue patch* | | | U test |
|---|---|---|---|---|---|
|  |  | + | ± | − |  |
| Physiological saline |  | 5 | 0 | 0 |  |
| Plipastatin A$_1$ | 590 | 0 | 0 | 5 | P < 0.05** |
| Plipastatin A$_1$ | 59 | 0 | 1 | 4 | P < 0.05 |
| Plipastatin A$_1$ | 5.9 | 2 | 3 | 0 | N. S.*** |
| DSCG | 590 | 0 | 1 | 4 | P < 0.05 |
| DSCG | 59 | 0 | 1 | 4 | P < 0.05 |

*The numbers of animals having the patch in a group of five animals.
**P Risk factor
***N.S. Not significant As shown in Table 4, the intradermal injections of 590 and 59 μM Plipastatin A$_1$ cause suppressive effects on PCA reactions that are comparable to those of DSCG. These data support the fact that the compound exhibits suppressive effects on type I allergic disorders such as asthma, pollinosis and atopic dermatitis.

As is clear from the experiments set forth above, Plipastatin of the present invention has suppressive effects on the cell-mediated immunity as well as relatively low toxicities, so it will be useful as a immunosuppressive agent having a different mechanism of action from conventional immunosuppressive drugs. In addition, Plipastatin exhibits suppressive effects on PCA reactions, so it will also be useful as an anti-allergic agent.

The present invention will be further illustrated by the following examples which are not intended to limit the scope of the present invention, and it will be apparent to those skilled in the art that various changes and modifications may be made without departing from the spirit or scope of the invention.

EXAMPLE 1

A medium (pH 7.4) comprising 2.5% glycerin, 0.5% of beef extract (product of Kyokuto K.K.), 0.5% of polypeptone, 1.0% of yeast extract (product of Oriental K.K.), 0.2% of NaCl, 0.05% of MgSO$_4$.7H$_2$O, 0.05% of K$_2$HPO$_4$, 0.32% of CaCO$_3$, 0.05% of a 1:1 mixture of Silicon KM-70 (product of Shin-etsu Kagaku K.K.) and soybean oil (JP) a an antifoaming agent was sterilized in an autoclave at 120° C. for 20 minutes. To a 500 ml Erlenmeyer flask was charged a 120 ml-portion of the sterilized medium which was inoculated with a loop of the Plipastatin-producing strain (FERM BP-934). The inoculated medium was incubated at 27° C. for a day on a rotary shaker (180 rpm). A 1 ml-portion of the seed culture thus obtained was transferred into a 500 ml Erlenmeyer flask containing 120 ml of said sterilized medium and cultivated with shaking for a day under the same conditions as set forth above. The cultured broth was filtered at pH 7.4 to remove the cells and obtain 18 l of a filtrate. The $IC_{50}$ value of the filtrate for the inhibition of phospholipase D was 32 μg/ml. The filtrate was passed through a column packed with Amberlite XAD-7 (2 l) to adsorb any enzyme inhibiting substance. The column was then washed with water (8 l) and eluted with 80% methanol (4 l) to collect fractions containing the active material. The combined fractions were concentrated under reduced pressure to dryness to give 24.6 g of brown crude powder having an $IC_{50}$ value of 18 μg/ml.

A solution of thus obtained crude powder in n-propanol was passed through a silica gel (1 l) column filled preliminarily with n-propanol, followed by successive elution with n-propanol (800 ml), 90% n-propanol solution (2 l) and 80% n-propanol solution (2.5 l) to collect the fractions containing the active substances, which were concentrated under vacuum to dryness. A brown powder (2.15 g) containing Plipastatin $B_1$ and $B_2$ $IC_{50}=15$ μg/ml) was obtained from the 90% n-propanol eluted fractions, and 2.0 g of a yellowish brown powder containing Plipastatin $A_1$ and $A_2$ =($IC_{50}=9.5$ μg/ml) from the 80% n-propanol eluted fractions. The yellowish brown powder of Group A thus obtained was passed through a column of silanised silica gel (400 ml) preliminarily filled with a 6:4 mixture of methanol and acetate buffer (1% potassium acetate plus 3% acetic acid, pH 5), followed by elution with the same mixture to collect the fractions containing the active substance. The combined fractions were then concentrated under reduced pressure to dryness. The resulting solid was dissolved in a small amount of 80% methanol and the solution was subjected to desalting for removal of excess potassium acetate on a column of Sephadex LH-20 that was eluted with 80% methanol. The fractions containing the active substances were collected and concentrated under reduced pressure to dryness to give 994 mg of a pale yellow powder ($IC_{50}=9.5$ μg/ml). The powder so obtained was passed through a column for High Pressure Liquid Chromatography (HPLC) (product of Senshu Kagaku K.K.; Nucleosil 5 $C_{18}$ 20 $\phi \times 300$ m/m; flow rate: 8 ml/min) preliminarily equilibrated with a 1:1 mixture of acetonitrile and acetate buffer (2% potassium acetate plus 6% acetic acid, pH 4), followed by elution with said equilibrating fluid to collect the fractions containing each of Plipastatin $A_1$ and $A_2$. The respective fractions were then concentrated to dryness and the resulting solids were desalted by the same method as used for desalting the eluate from the silanised silica gel column, thereby giving 542 mg of Plipastatin $A_1$ ($IC_{50}=2.1$ μg/ml) as a colorless powder and 152 mg of Plipastatin $A_2$ ($IC_{50}=3.8$ μg/ml), also as a colorless powder.

The yellowish brown powder containing Group B ($B_1$ and $B_2$) substance of the present invention obtained from the 90% n-propanol eluting fractions was also passed through a column of silanised silica gel (200 ml) preliminarily filled with 40% methanol, followed by successive elution with 40% methanol (1.5 l) and 60% methanol (1.5 l) to collect the fractions containing the active substances. The combined fractions were then concentrated to dryness. The residue was dissolved in a small amount of 80% methanol and the resulting solution was passed through a column of Sephadex LH-20, followed by elution with 80% methanol to collect the fractions containing the active substances which were then concentrated to dryness to give 545 mg of a pale yellow powder ($IC_{50}=8$ μg/ml). The powder so obtained was then passed through a column for HPLC (Nucleosil 5 $C_{18}$20 $\phi \times 300$ m/m; flow rate: 8 m/min) preliminarily equilibrated with a 65:35 mixture of acetonitrile and acetate buffer (2% potassium acetate plus 6% acetic acid, pH 4), followed by elution with said equilibrating fluid to collect the fractions containing each of Plipastatin $B_1$ and $B_2$. The respective fractions were concentrated to dryness. The residues were desalted by eluting them with 80% methanol from a column of Sephadex LH-20 to give 151 mg of Plipastatin $B_1$ ($IC_{50}=2.8$ μg/ml) as a colorless powder and 89 mg of Plipastatin $B_2$ ($IC_{50}=3.3$ μg/ml), also as a colorless powder.

Reference Example 1

The following chemical experiments and instrumental analysis were conducted in order to determine the structure of the fatty acids constituting the substances of the present invention.

Plipastatin $A_1$ or $B_1$ of the present invention was subjected to methanolysis in a 30% HCl/methanol at 50° C. for 2 days and then concentrated to dryness. The resulting residue was extracted with diethyl ether. The extract was subjected to thin layer chromatography (hereunder referred to as TLC) on silica gel [developing solvent: chloroform/methanol (50:1)] to separate the methanolysis product. The instrumental analysis of the product with NMR and MS showed that the fatty acid constituting Plipastatin $A_1$ and $B_1$ of the present invention is β-hydroxy hexadecanoic acid (β-hydroxy palmitic acid).

In the same manner as set forth above, the fatty acid composing Plipastatin $A_2$ and $B_2$ of the present invention was determined as β-hydroxy anteisohexadecanoic acid (β-hydroxy anteisopalmitic acid).

Reference Example 2

The following enzymatic and chemical analysis were made to determine the tyrosine and C-end isoleucine which form the lactone ring of the present invention.

The inhibitors of the present invention were digested with carboxypeptidase Y in accordance with the following two methods and the amino acid liberated by the digestion was examined. Carboxypeptidase Y has the ability to successively cleave an amino acids sequence from its end to liberate a C-end amino acid.

(i) Direct digestion by the enzyme without any pretreatment; or (ii) Enzymatic digestion after opening the lactone ring of the inhibitors with an alkali.

The following two results occur after conducting Enzymatic digestion by the above-mentioned two methods:

(i) No free amino acid detected; or (ii) Ile, Tyr and Gln were liberated in that order.

On the basis of these data, the present inventors confirmed that the C-end amino acid is Ile and that the lactone is formed at the C-end.

The functional groups capable of forming the lactone ring with the C-end Ile are the hydroxy groups of the fatty acid, of the two Tyrs and of the Thr. When the inhibitors of the present invention were subjected to acetylation with acetic anhydride in a solution of pyridine, the hydroxy groups of the fatty acid, Thr, and Tyr linked to Ile were acetylated, as confirmed by the NMR and MS spectra of the acetyl derivatives obtained.

These results demonstrate that the C-end Ile forms lactone with phenyl hydroxy group of the tyrosine connected with ornithine.

What is claimed is:

1. A compound of the following general formula:

wherein $R_1$ is $-C_{13}H_{27}$ or $-C_{14}H_{29}$; and $R_2$ is Ala or Val, or salts thereof.

2. A compound according to claim 1, wherein $R_1$ is $-C_{13}H_{27}$ or salts thereof.

3. A compound according to claim 1, wherein $R_1$ is $-C_{14}H_{29}$ or salts thereof.

4. Plipastatin $A_1$ represented by the following formula

CH$_3$(CH$_2$)$_{12}$CHCH$_2$CO—Glu—Orn—
  |
  OH

5. Plipastatin $A_2$ represented by the following formula

6. Plipastatin $B_1$ represented by the following formula

CH$_3$(CH$_2$)$_{12}$CHCH$_2$CO—Glu—Orn—
  |
  OH

—Tyr—Thr—Glu—Val—Pro—Gln—Tyr—Ile
  |_____________O_____________|

7. Plipastatin $B_2$ represented by the following formula

* * * * *